US009581494B2

(12) United States Patent
Weiβ et al.

(10) Patent No.: US 9,581,494 B2
(45) Date of Patent: Feb. 28, 2017

(54) METHOD AND DEVICE FOR ANALYZING SMALL PARTICLES IN GAS

(71) Applicant: Pala GmbH Partikel- und Lasermeβtechnik, Karlsruhe (DE)

(72) Inventors: Maximilian Weiβ, Weingarten (DE); Leander Mölter, Wörth am Rhein (DE)

(73) Assignee: PALAS GmbH Partikel- und Lasermeβtechnik, Karlsruhe (DE)

( * ) Notice: Subject to any disclaimer, the term of this patent is extended or adjusted under 35 U.S.C. 154(b) by 247 days.

(21) Appl. No.: 14/042,829

(22) Filed: Oct. 1, 2013

(65) Prior Publication Data

US 2014/0092386 A1 Apr. 3, 2014

(30) Foreign Application Priority Data

Oct. 2, 2012 (DE) ........................ 10 2012 019 383
Oct. 11, 2012 (DE) ........................ 10 2012 019 926

(51) Int. Cl.
*G01J 3/18* (2006.01)
*G01N 21/27* (2006.01)
(Continued)

(52) U.S. Cl.
CPC ............. *G01J 3/18* (2013.01); *G01N 15/1425* (2013.01); *G01N 15/1459* (2013.01);
(Continued)

(58) Field of Classification Search
CPC .............. G01N 15/1425; G01N 21/274; G01N 15/1459; G01N 21/53; G01N 2015/0046; G05B 6/00; G05B 19/00; G01J 3/18
(Continued)

(56) References Cited

U.S. PATENT DOCUMENTS 4,929,079 A 5/1990 Delfour et al.
2004/0011975 A1 1/2004 Nicoli et al.
(Continued)

FOREIGN PATENT DOCUMENTS

DE 690 28 687 T2 4/1997
DE 197 24 228 A1 12/1998
WO 2009/021123 A1 2/2009

OTHER PUBLICATIONS

Kreibig, Uwe et al.: Interfaces in Nanostructures: Optical Investigations on Cluster-Matter. In: NanoStructured Materials, vol. 11, No. 8, 1999, pp. 1335-1342.

*Primary Examiner* — Kara E Geisel
*Assistant Examiner* — Dominic J. Bologna
(74) *Attorney, Agent, or Firm* — McGlew and Tuttle, P.C.

(57) ABSTRACT

A method for detecting decalibration of a device for analyzing particles, including irradiating particles with light, detecting light scattered from the particles, amplifying, digitizing and detecting the electric signal obtained in a plurality of digital channels corresponding to the intensity representing the particle size and monitoring the appearance of the Mie peak in the measured size-dependent frequency distribution and sending a report if the Mie peak deviates in a digital channel other than the digital standard channel belonging to it based on measurement settings. The electronic analyzing unit detecting a Mie peak in the measured particle size distribution and assigning it to a digital detection channel in a device for detecting the concentration of small particles in gas, with a sample tube, a light source, a detector detecting scattered light scattered on the particles, an analog amplifier, an analog-digital converter, an electronic analyzing unit and a display and operating unit.

20 Claims, 3 Drawing Sheets

(51) Int. Cl.
*G01N 21/53* (2006.01)
*G01N 15/14* (2006.01)
*G01N 15/00* (2006.01)

(52) U.S. Cl.
CPC ........... *G01N 21/274* (2013.01); *G01N 21/53* (2013.01); *G01N 2015/0046* (2013.01)

(58) Field of Classification Search
USPC .................................................. 356/337–339
See application file for complete search history.

(56) References Cited

U.S. PATENT DOCUMENTS

2008/0319680 A1* 12/2008 Fox et al. ....................... 702/21
2009/0039249 A1* 2/2009 Wang et al. .................. 250/287
2009/0190129 A1* 7/2009 Yguerabide et al. ......... 356/338
2010/0288921 A1* 11/2010 Wang et al. .................. 250/287
2014/0358447 A1* 12/2014 Doyle et al. .................... 702/19

* cited by examiner counts
channel
P'
P
M
N_k

METHOD AND DEVICE FOR ANALYZING SMALL PARTICLES IN GAS

CROSS REFERENCE TO RELATED APPLICATIONS

This application claims the benefit of priority under 35 U.S.C. §119 of German patent application DE 10 2012 019 383.1 filed Oct. 2, 2012 and German patent application DE 10 2012 019 926.0 filed Oct. 11, 2012, the entire contents of each application are incorporated herein by reference.

FIELD OF THE INVENTION

The present invention pertains to a method for analyzing small particles in gas, wherein the particles are irradiated with light, light scattered by the particles is detected, the electric signal obtained is amplified, digitized and detected in a plurality of digital channels corresponding to the intensity representing the particle size, as well as to a device for analyzing small particles in gas, with a sample tube, a light source irradiating same, a detector for detecting scattered light scattered on the particles, an analog amplifier, an analog-digital converter, an electronic analyzing unit and a display and operating unit.

Such a device is known as a fine dust emissions monitoring system and aerosol spectrometer and makes possible the continuous and simultaneous detection of the concentration of particles in gas (the count of these particles in a preset volume of space), especially in air, based on the particle size, and hence the detection of characteristic values, such as $PM_{2.5}$ and $PM_{10}$.

BACKGROUND OF THE INVENTION

Such prior-art devices are based on the principle of optical light scattering and have a light source with high light stability, especially as an LED light source with long service life. The air carrying particles is sent via a sampling head through a sample tube, in which the sample is irradiated by the light at a finite angle relative to the direction of flow of the medium, usually at right angles hereto (i.e., at an angle not equal to 0°), such as preferably between 10° and 170°, preferably in the range of 80° to 100° relative to the direction of irradiation of the light.

The aerosol sensor is an optical aerosol spectrometer, which determines the particle size on the basis of scattered light analysis on the individual particle.

A defined gas volume flow is generated (in the range of 1.2 $dm^3$/minute to 2.3 $m^3$/hour) by means of a pump drawing in gas/air from the environment. The particles are moving individually through an optically defined measuring volume, which is illuminated homogeneously. A scattered light pulse, which is detected at the angle mentioned, is generated by every individual particle. The particle count is measured on the basis of the scattered light pulses. The particle concentration (e.g., particles per $cm^3$) is calculated from the measured particle flow relative to the known volume flow (e.g., $m^3$/sec). The level of the scattered light pulses is an indicator of the particle diameter.

Accordingly, each scattered light pulse is detected and assigned to a particle size based on its intensity, and the particle sizes of a plurality of channels, for example, 256 channels, are classified in a digital measuring system.

Such devices may have, furthermore, drying sections as well as sensors for detecting temperature, air pressure and relative humidity in order to thus rule out a distortion of measurement results due to condensation effects. Moisture compensation is carried out depending on the relative humidity of the air and the outside temperature.

Such a device for detecting the particle count concentration operates reliably and satisfactorily. However, the inner wall of the sample tube, through which the particle-containing gas to be analyzed flows, may become contaminated and cloudy due to the deposition of particles, so that the measuring means becomes decalibrated hereby. This means that smaller particles are actually counted in a measuring channel, which is intended for a certain particle size range, due to the attenuation of the scattered radiation that is caused by this.

SUMMARY OF THE INVENTION

A basic object of the present invention is therefore to perfect a method and a device of the type mentioned in the introduction such that such a decalibration can be detected and recalibration can be performed in a suitable manner.

This object is accomplished according to the present invention with a method of the type mentioned in the introduction such that the appearance of a peak, the "Mie peak," in the size-dependent frequency distribution measured is monitored and a report is sent when this Mie peak appears in one or more channels other than the one or more of the at least one digital standard channel belonging to it based on the measurement settings. According to the present invention, a device of this class provides for a means for monitoring the appearance of a peak in the measured size-dependent frequency distribution, of the Mie peak, and for sending a report in case of a deviation of the Mie peak in at least one digital standard channel other than that belonging to it based on the measurement settings. An analyzing unit is designed, further, for detecting a peak, the Mie peak, in the measured particle size distribution and for assigning same to at least one digital detection channel (standard channel).

The method according to the present invention is carried out especially on the basis of a measurement carried out by means of a device of this class.

The present invention thus utilizes the fact that in case of particles whose size approximately corresponds to the wavelength of light (more accurately $\pi d \sim \lambda$, wherein d is the particle diameter, $\lambda 0$ is the wavelength of light), the more accurate particle count concentration distribution does not show the expected monotonic drop, but an irregularity in the form of a flattening or a peak in the flank of the declining particle count concentration distribution based on the Mie effect, so that this peak is called "Mie peak" here. It is checked—automatically—according to the present invention whether this irregularity, especially such a peak in the flank is located in the standard channel provided for the corresponding particle diameter in case of digital detection or whether it migrates in a channel, which shall per se detect particles whose size is smaller than the size (diameter) and smaller than the range of the wavelength of the irradiated light. If the latter is true, this is an indicator of a decalibration of the system based on the above-mentioned contamination, especially of the optical system, such as lenses, etc., upon which suitable actions can be taken for recalibration, either manually or automatically, such as increasing the gain of the analog amplifier of the system in a certain range or else increasing the irradiated light intensity or, in case of advanced contamination and hence decalibration, cleaning of the sample tube, in order to restore the initial state.

The light used is preferably not white light but colored light, especially also monochromatic or narrow-band light, because the above-described Mie peak appears clearly visible in such light only. It was found to be extremely preferable to use blue light as the light color and/or a wavelength band of ±100 nm, preferably ±50 nm, around a mean wavelength of the colored light, for example, 450 nm. A corresponding, blue light-emitting diode is preferably used.

Provisions may be made in another preferred embodiment for sending a corresponding acoustic or optical warning signal if a comparison of the particle count concentration in the corresponding channels shows that the particle count concentration is lower in the standard channel provided for particles with a size in the range of the wavelength of the light than in the directly adjacent channel intended for smaller particle diameters and/or that the particle count concentration in this channel is greater than that in this adjacent channel intended for even smaller particles.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
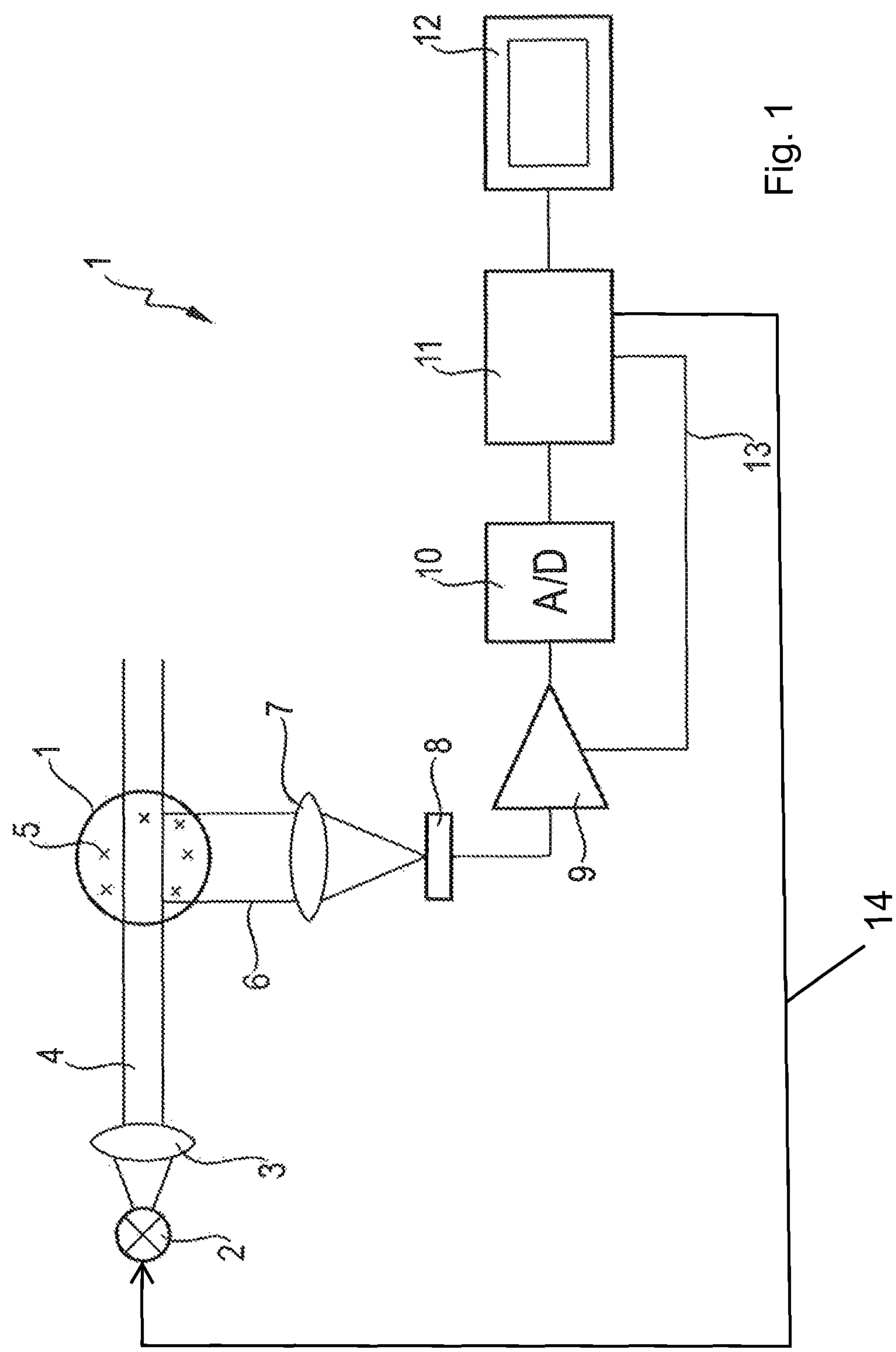
FIG. 1 is a schematic view of a device according to the present invention.

The device 1 according to the present invention has essentially the following elements: A light source 2, preferably in the form of a monochromatic light-emitting diode—LED—sends light via an optical system 3 (convergent lens) through a sampling tube 1 connected to a sampling head (not shown). The scattered light 6 scattered on the particles 5 in the sample tube 1 is detected by a detector 8 via an optical system 7 (convergent lens) and the optical system 7 and the detector 8 are arranged at equal axial height of the sampling tube 1 as the optical system 3 and the light source 2. Detection takes place in the exemplary embodiment being shown at an angle of about 85° to 95° relative to the direction of the incidence light beam 4. Detector 8 is followed by an analog amplifier 9, which is in turn followed by an analog-digital converter 10. This is joined by an evaluation electronics 11, and the latter is in turn followed by a display and operating unit 12.

Furthermore, a feedback path 13 is provided between the evaluation electronics 11 and the analog amplifier 9 in order to bring about a change in the gain of amplifier 9 on the basis of the analysis performed in the evaluation electronics 11. A feedback path 14 is provided between the evaluation electronics 11 and the light source 2 in order to bring about a change in the intensity of the light source 2 on the basis of the analysis performed in the evaluation electronics 11.

Figure 2:
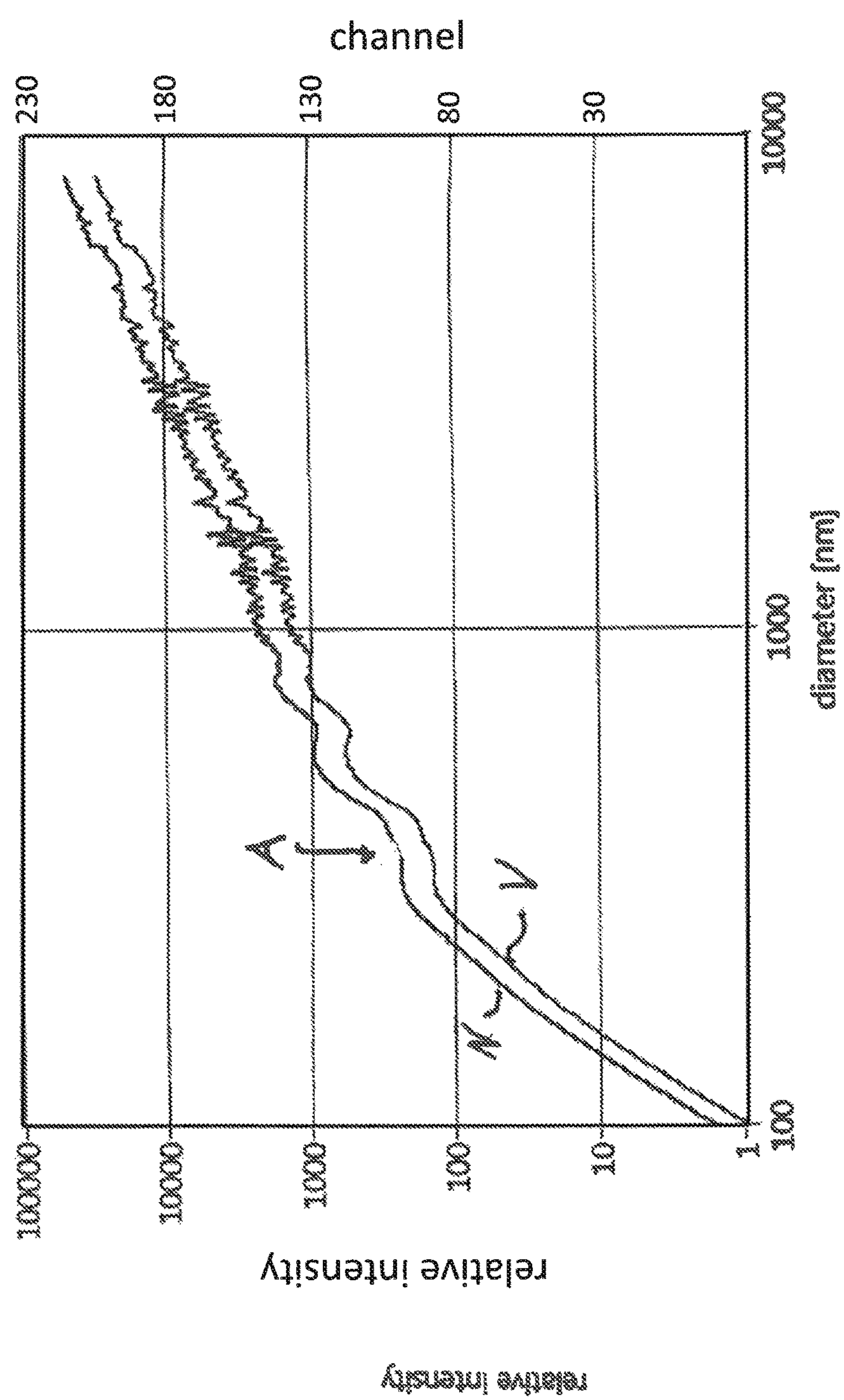
FIG. 2 is a qualitative view of the scattering intensity over the particle size.

FIG. 2 shows qualitatively the scattering intensity of the light scattering on particles over the particle size according to the Mie theory for the device according to the present invention. The irradiation is carried out with narrow-band light of a diode emitting blue light (LED) with a mean value of the wavelength at 450 nm (corresponding to 0.45 μm) with a variance of about 50 nm. It is also possible to use, in principle, other light sources meeting these requirements, such as LEDs emitting other colors, also with a broader spectrum, or even lasers.

The relative intensity (ordinate) of the light scattered on a particle of a known size is plotted over different particle sizes (abscissa). The detection of the scattered light is provided in the exemplary embodiment shown at the angle of about 90° mentioned already relative to the direction of irradiation or in the range of 85° to 95° relative to the direction of irradiation.

The upper intensity curve N shown in FIG. 2 is obtained. This has a steep slope in case of particle sizes that are small compared to the wavelength of the light, namely, 450 nm. The slope is proportional in this range to the sixth power of the particle size. Increased light scattering is obtained in the forward direction in case of particle sizes in the range of the wavelength of the light because of the Mie effect, so that the intensity of the scattered radiation recorded at the angle becomes flatter and does not rise or shows hardly any rise ("Mie plateau"). This flattening is seen as a Mie plateau. The intensity of the scattered light increases again in the recording direction (doing so with the second power of the particle size) only at particle sizes that are large compared to the wavelength of the irradiated light.

If the exiting scattered radiation is attenuated (and so is possibly the entering radiation), for example, because of the deposition of particles on the inside of the sample tube, the intensity of the scattered radiation received decreases and a curve V is obtained, which extends essentially equidistantly (in the ordinate direction) below a standard intensity curve N (FIG. 2).

The intensity values are assigned during their digitization provided by the analog/digital converter 10 in a certain range to a preset plurality of channels, for example, 256 channels (corresponding to $2^8$ or an 8-bit-long or 1-byte-long "word"); a smaller number of channels may be provided as well. The size resolution of the detection of the particles is low in the range of the above-described "Mie plateau" or Mie flattening, i.e., particles are assigned to a channel in a broader size range than below and above the flattening, so that a larger percentage of particles than would correspond to the actual size distribution is detected in the corresponding standard channel than would for this reason alone.

Figure 3:
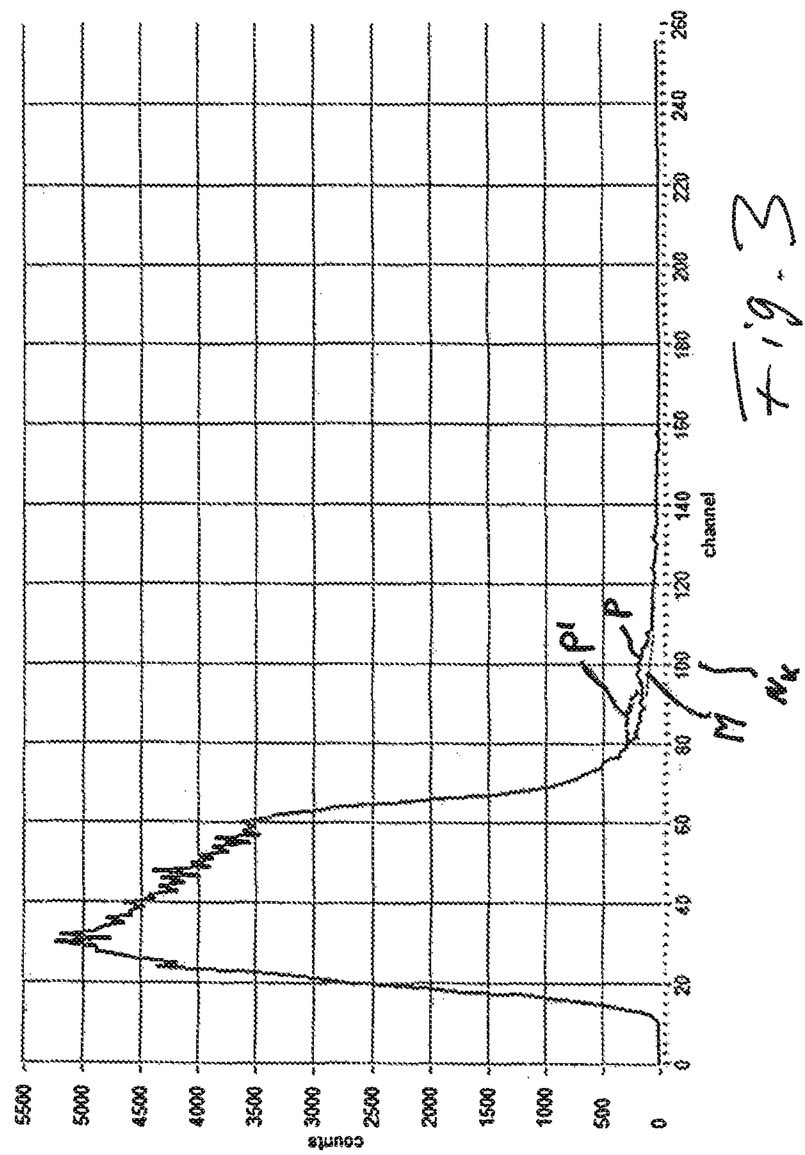
FIG. 3 is a qualitative view of a fine dust measurement with the particle count over the channels of a digital detection means representing the particle size.

The digital measuring channels detecting the respective scattering intensities, which channels correspond to the channels shown on the abscissa in FIG. 3, are assigned to the respective scattering intensities on the ordinate on the right-hand side in FIG. 2. What is measured is the frequency of scattered light pulses (of individual particles) of a known intensity each in the associated channel (as an indicator of the size of the particle), the count determined in each channel now being an indicator of the number of particles of the corresponding size.

FIG. 3 shows a measurement diagram of a digital fine dust-measuring system, in which particles of different sizes are present in a natural or usual distribution and hence with a larger number of small particles and with a lower number of larger particles. The drop in the frequency of occurrence of the number of small particles to that of the large particles plausibly takes place monotonically with the particle size. Based on the individual scatter values, these are always classified, corresponding to FIG. 2, to a corresponding channel. The number or frequency shown on the ordinate is obtained by adding up the individual measurement results for the respective channel over a certain time period.

It is seen now that the frequency curve shown in FIG. 3 does not have, as was stated above, the monotonically dropping shape, to be expected per se (indicated by M with broken line in FIG. 3) in the range of at least one of the channels, in which the particles whose size is in the range of the wavelength of the irradiated light are detected, but it rather has a slight peak there, which shall be called "Mie peak" P for short. This peak is due solely to the physical effect of the scattering characteristic of particles of a size in the range of the wavelength of the light, which effect is represented with reference to the flattening or the "Mie plateau" A in FIG. 2.

If dust particles are deposited on the inside of the sample tube, the scattering intensity of the individual scattering is reduced, as is shown with reference to FIG. 2, from curve N there to V, which causes the Mie peak in FIG. 3, which is present in the area of the flattening A of the curve in FIG. 2, to migrate as P' to channels intended for the detection of particles of a smaller size. This shows a decalibration of the system.

The flattening A of the calibration curve also occurs, in a somewhat weaker form, at larger particle diameters and can be used as well. However, this effect is most pronounced in the range of the wavelength of the light.

This is detected according to the present invention by the evaluation electronics 11 by the particle count detected being compared in the standard channel K assigned to the "Mie peak" to the counts in adjacent channels, especially the directly adjacent channels for smaller particle sizes. If it is determined, for example, that the particle count in channel $N_k$ is no longer greater than that in channel $N_{k-1}$, but that in channel $N_{k-1}$ is greater than that in channel $N_{k-2}$, the corresponding values can be displayed on the display and operating unit 12, on the one hand, and the information for a manual action can be given to the operator. Acoustic or optical warning signals can also be sent during the automatic comparison in case of the deviations from the standard values; moreover, there may also be a reaction to the amplifier or to the intensity of illumination of the light source to the amplifier 9 or even to the light intensity of the light source 2 in order to restore a recalibration, i.e., there is amplification until the Mie peak P moves again into the standard channel $N_k$. An automatic electronic recalibration in this manner can be performed in a certain narrow range only. This may also be performed manually by an operator. If the deviations become too great, cleaning of the sample tube is prompted.

While specific embodiments of the invention have been shown and described in detail to illustrate the application of the principles of the invention, it will be understood that the invention may be embodied otherwise without departing from such principles.

What is claimed is:

1. A method for analyzing small particles in gas, the method comprising:
- irradiating particles with light;
- detecting light scattered by the particles;
- amplifying, digitizing and detecting an electric signal in a plurality of digital channels as a measured size-dependent frequency distribution corresponding to an intensity representing a particle size of said particles, said electric signal being obtained based on detection of said light scattered by said particles;
- monitoring an appearance of a peak or flattening in a flank of said measured size-dependent frequency distribution and providing a report if said peak appears in one or more digital channels other than at least one standard channel belonging to said peak based on measurement settings in order to provide a recalibration, wherein the peak or flattening of said flank of said measured size-dependent frequency distribution is different from a maximum of said measured size-dependent frequency distribution.

2. A method in accordance with claim 1, wherein the particles are irradiated with colored light.

3. A method in accordance with claim 2, wherein the particles are irradiated with a blue light-emitting diode.

4. A method in accordance with claim 1, wherein the particles are irradiated with a bandwidth of +100 nm, around a mean wavelength of the light.

5. A method in accordance with claim 4, wherein the particles are irradiated with a bandwidth of +50 nm, around a mean wavelength of the light, wherein the mean wavelength is in a blue range.

6. A method in accordance with claim 1, further comprising:
- providing an operation bringing about said recalibration of a measuring means when the peak deviates from the at least one standard channel, wherein said peak or flattening is on a falling or decreasing flank of said measured size-dependent frequency distribution.

7. A method in accordance with claim 6, wherein a gain of an analog amplifier is increased in a defined manner such that the peak appears again in the at least one standard channel.

8. A method in accordance with claim 6, wherein a light intensity of a light-emitting diode is increased in a defined manner such that the peak appears again in the at least one standard channel.

9. A method in accordance with claim 6, wherein cleaning of the measuring means is performed.

10. A method in accordance with claim 6, wherein the recalibration is carried out automatically.

11. A device for analyzing small particles in gas, the device comprising:
- an irradiation means for irradiating particles with light such that the light is scattered by the particles;
- a detecting means for detecting the light scattered by the particles, wherein an electric signal is obtained based on detection of the light scattered by the particles;
- a plurality of channels, wherein said electric signal is amplified, digitized and detected in said plurality of digital channels as a measured size-dependent frequency distribution corresponding to an intensity representing particle size;
- evaluation electronics for monitoring an appearance of a peak or flattening in a flank of said measured size-dependent frequency distribution and for sending a report if said peak deviates in a digital channel other than at least one digital standard channel belonging to said peak based on measurement settings in order to recalibrate the device, wherein the peak or flattening in said flank of said measured size-dependent frequency distribution is different from a maximum of said measured size-dependent frequency distribution.

12. A device in accordance with claim 11, further comprising:
- a sample tube, said irradiation means comprising a light source, said light source irradiating said sample tube, said detecting means comprising a detector for detecting scattered light scattered on the particle;
- an analog amplifier;

an analog-digital converter; and a display and operating unit, said evaluation electronics detecting a peak in the measured-size dependent frequency distribution and said analyzing unit assigning said peak to at least one digital detection channel, said evaluation electronics detecting the peak in the flank of the measure size-dependent frequency distribution.

13. A device in accordance with claim 12, wherein said at least one digital detection channel is said at least one digital standard channel, wherein said peak or flattening is on a falling or decreasing flank of said measured size-dependent frequency distribution.

14. A device in accordance with claim 12, wherein said light source emits colored light.

15. A device in accordance with claim 13, wherein said light source is a blue LED.

16. A device in accordance with claim 12, further comprising:

an optical or acoustic signal means for displaying the appearance of the peak in a channel other than said at least one digital standard channel.

17. A device in accordance with claim 12, further comprising:

a feedback path for recalibration by increasing one or more of a gain of the analog amplifier and a light intensity of the light source to an extent that the peak appears again in the at least one digital standard channel.

18. A method for analyzing small particles in gas, the method comprising:

providing a device for analyzing particles, said device comprising a light source;

irradiating particles with light from said light source;

detecting light scattered by the particles;

providing at least one signal based on detection of said light scattered by said particles, said at least one signal comprising a measurement of an intensity of said light;

providing said at least one signal to a plurality of digital channels;

amplifying and digitizing said at least one signal to provide a measured size-dependent frequency distribution, said measured size-dependent frequency distribution corresponding to a particle size of said particles based on said measurement of said intensity of said light;

determining whether one of a peak occurs in said measured size-dependent frequency distribution of at least one standard channel of said plurality of digital channels and a flattening of a flank of said measured size-dependent frequency distribution of said at least one standard channel of said plurality of digital channels;

providing a notification as output if said one of said peak and said flattening of said flank of said measured size-dependent frequency distribution is detected in one or more digital channels other than said at least one standard channel;

recalibrating said device if said one of said peak and said flattening of said flank of said measured size-dependent frequency distribution is detected in said one or more digital channels other than said at least one standard channel.

19. A method in accordance with claim 18, wherein said light source emits colored light, said light source comprising a blue light-emitting diode.

20. A method in accordance with claim 18, wherein said device comprises a sample tube and an analog amplifier, wherein recalibrating said device comprises one or more of increasing a gain of said analog amplifier in a predetermined range, increasing an irradiated light intensity from said light source and cleaning said sample tube, wherein the peak or flattening of said flank of said measured size-dependent frequency distribution is different from a maximum of said measured size-dependent frequency distribution, wherein said peak or flattening is on a falling or decreasing flank of said measured size-dependent frequency distribution.

* * * * *